United States

Harsch

4,039,803

Aug. 2, 1977

[54] ELECTRO-OPTIC WELDING HELMET LENS ASSEMBLY

[75] Inventor: Thomas B. Harsch, Stow, Ohio

[73] Assignee: Mack Gordon, Cleveland, Ohio

[21] Appl. No.: 674,903

[22] Filed: Apr. 8, 1976

[51] Int. Cl.² .............................................. B23K 9/32
[52] U.S. Cl. .......................................... 219/147; 2/8; 350/160 LC
[58] Field of Search ............................. 250/338, 340; 350/160 LC; 219/147; 2/8

[56] References Cited

U.S. PATENT DOCUMENTS

| | | | |
|---|---|---|---|
| 3,159,844 | 12/1964 | Haboush | 2/8 |
| 3,748,471 | 7/1973 | Ross | 250/340 |
| 3,873,804 | 3/1975 | Gordon | 219/147 |

FOREIGN PATENT DOCUMENTS

| | | | |
|---|---|---|---|
| 2,315,308 | 10/1973 | Germany | 2/8 |

*Primary Examiner*—E. A. Goldberg
*Attorney, Agent, or Firm*—Brown, Murray, Flick & Peckham

[57] ABSTRACT

A protective welding lens assembly for use as the eyepiece of a welding helmet. The lens assembly utilizes a liquid crystal light shutter together with an electrical circuit adapted to change the light shutter from a uniform light-transmitting condition to a uniform, approximately opaque condition of very small light transmission solely in response to light energy emitted by an electric welding arc without the use of any connecting wires. Two light sensing devices are employed, one of which responds to visible light only and the other of which responds to infrared wave energy only. In order to change the light shutter from a light-transmitting to an opaque condition, both the visible and infrared wave energies from the arc must be sensed. This prevents a condition wherein the light shutter will remain opaque, even after the welding arc is extinguished, due to emission of infrared wave energy from a still-hot weld bead.

5 Claims, 5 Drawing Figures

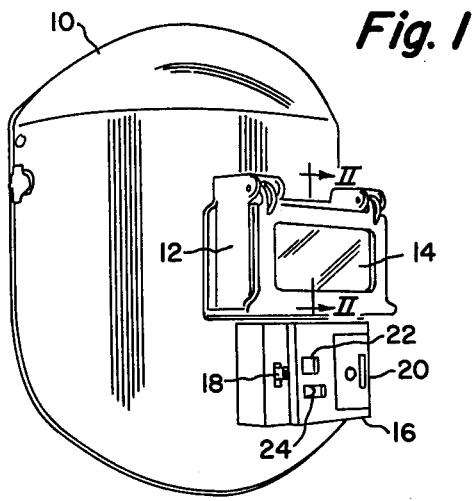
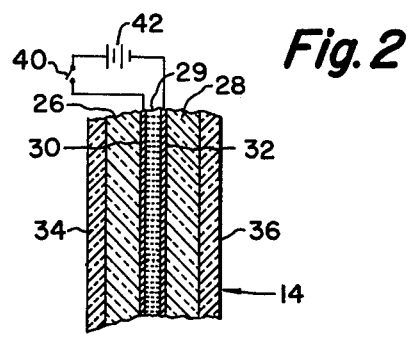
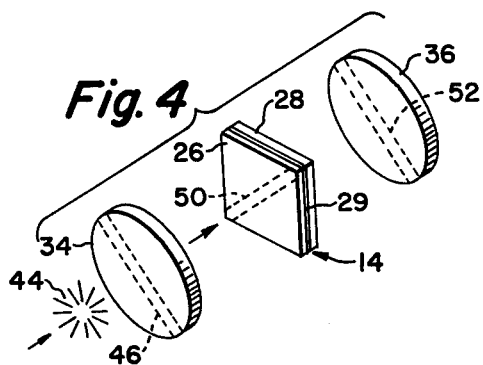
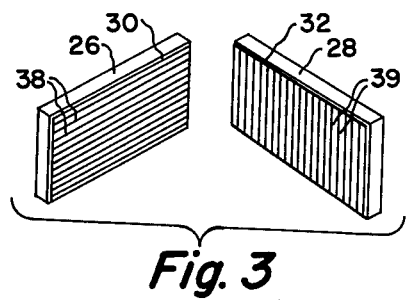
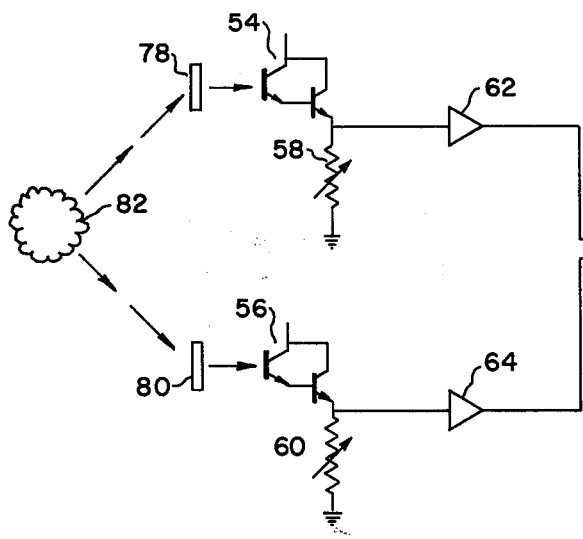

ELECTRO-OPTIC WELDING HELMET LENS ASSEMBLY

BACKGROUND OF THE INVENTION

In U.S. Pat. No. 3,873,804 a welder's helmet is disclosed utilizing a protective welding lens assembly comprising a layer of nematic liquid crystal material sandwiched between opposing parallel plates coated with transparent conductive films. Polarizers are disposed on opposite sides of the plates such that by applying an electrical field across the transparent conductive films, the opacity of the liquid crystal light shutter can be changed.

In one embodiment of the invention shown in the aforesaid U.S. Pat. No. 3,873,804, light energy is sensed from the welding arc by means of a phototransistor or the like in order to cause the liquid crystal light shutter of the lens assembly to change from a light-transmitting condition, wherein the welder can view the work as illuminated by ambient light, to a substantially opaque condition when the arc is struck, the opaque condition being such as to transmit less than 1% of the visible light.

While a phototransistor of the type described above is a convenient means of detecting the existence of a welding arc, such an arc is a small portion of the field of view of the phototransistor comprising the area viewed by the welding helmet user. In this respect, visible light energy from the welding arc, at a distance of a few feet, is generally one and not more than ten times the magnitude of the ambient illumination in a welding shop and often less than one. As a result, detecting the visible light from the welding arc is not a satisfactory means of triggering the light shutter into a substantially opaque condition.

The liquid crystal light shutter of a welding helmet can be triggered into a substantially opaque condition by infrared wave energy prevalent in the welding arc but not present in fluorescent illumination, the most common illumination for welding shops. However, this also presents problems for the reason that when the welding helmet is close to the arc, and after the arc is extinguished, a phototransistor responsive to infrared radiation will receive a detectable level of such infrared radiation from the still-hot welding bead. Consequently, the liquid crystal light shutter, which the infrared detector system controls, will not open for periods of several seconds and will remain substantially opaque after the arc is extinguished so that the welder cannot view the work under ambient illumination in a welding shop.

SUMMARY OF THE INVENTION

In accordance with the present invention, a control system for a liquid crystal light shutter embodied in a welding helmet lens assembly is caused to close or become substantially opaque only when an arc is struck and both infrared and visible wave energies are sensed. After the arc is extinguished, the light shutter will open since insufficient visible light will then be sensed, even though infrared wave energy is still emitted by a hot weld bead.

Specifically, there is provided in accordance with the invention, a control system for a liquid crystal light shutter welding helmet lens assembly comprising first means exposed to light emitted from a welding arc for producing a first electrical signal in response only to visible light from the arc, second means exposed to light emitted from a welding arc for producing a second electrical signal only in response to infrared wave energy from the arc, and circuitry coupled to the first and second means and operable only when both said first and second electrical signals are produced for increasing the opacity of the liquid crystal light shutter.

In the preferred embodiment of the invention, the first and second means exposed to light emitted from the welding arc comprise two phototransistors, one of which is provided with a filter which will pass visible light only and the other of which is provided with a filter which will pass infrared wave energy only. The outputs of the phototransistors are then applied to the input of an AND circuit such that an output will be produced from the AND circuit when, and only when, both visible and infrared wave energies are sensed to change the liquid crystal light shutter in the lens assembly from light transmitting to a substantially opaque condition.

The above and other objects and features of the invention will become more apparent from the following detailed description taken in connection with the accompanying drawings which form a part of this specification, and in which:

FIG. 1 is a perspective view of a welding helmet incorporating a liquid crystal light shutter assembly and the photodetector control system of the present invention;

FIG. 2 is an enlarged fragmentary sectional view taken along line II—II of FIG. 1;

FIG. 3 is a view illustrating the manner in which the transparent plates of the liquid crystal unit of FIG. 2 are rubbed at right angles with respect to each other;

FIG. 4 is a schematic illustration showing the manner in which polarized light passes through the liquid crystal unit of the lens assembly of FIG. 2; and FIG. 5 is a schematic circuit diagram of the control system of the invention for the liquid crystal unit of FIG. 2 utilizing two phototransistors, one of which is responsive to visible light only and the other of which is responsive to infrared wave energy only.

With reference now to the drawings, and particularly to FIG. 1, a welder's helmet 10 is shown provided with a window or lens assembly 12 having an eyepiece 14 comprising a liquid crystal light shutter hereinafter described with more particularity with reference to FIGS. 2, 3 and 4. Beneath the lens assembly 12 is an electronic unit 16 incorporating a manually-operated switch 18 which acts to switch the control system ON or OFF. As will be seen, when the control system is switched ON by the switch 18, the liquid crystal light shutter 14 will change from a substantially opaque to a light-transmitting condition such that the welder can see through the light shutter under ambient light conditions. However, should there be a power failure or failure of the electronic circuitry, the liquid crystal light shutter 14 will automatically become opaque, thereby protecting the welder's eyes against a possible malfunction of the circuitry or a power failure. The electronic unit 16 is provided with a door or flap 20 which can be opened to insert a battery into the unit. Unit 16 is also provided with two windows 22 and 24. Behind the windows 22 and 24 are phototransistors and light filters hereinafter described, one of which will pass visible light only and the other of which will pass infrared wave energy only.

With reference to FIG. 2, the details of the liquid crystal shutter are shown. It comprises a first transparent plate 26, preferably glass, and a second transparent plate 28, also of glass, and extending parallel to the plate 26. The plates 26 and 28 are spaced apart by suitable spacers, not shown. The space between the plates is filled with a nematic-phase liquid crystal material 29 with a positive dielectric anistropy, a suitable nematic-liquid crystal material being described in Fergason U.S. Pat. No. 3,918,796, issued Nov. 11, 1975.

Disposed on the interior surfaces of the transparent plates 26 and 28 are coatings 30 and 32 of thin transparent electroconductive material, such as the known tin oxide or indium oxide coatings. On the opposite sides of the two glass plates 26 and 28 are polarizers 34 and 36, these polarizers being polarized parallel to each other in the preferred embodiment of the invention.

With reference to FIG. 3, in the preparation of the liquid crystal light shutter, the glass plates 26 and 28 with the transparent conductive coatings 30 and 32 thereon are prepared by initially rubbing them unidirectionally with, for example, a cotton cloth. The direction of rubbing on the respective plates 26 and 28 is indicated by the lines 38 and 39 in FIG. 3; and it will be appreciated that the directions of rubbing on the respective plates are at right angles to each other. The effect of this is to produce a twisted nematic structure. In this respect, the molecules in the nematic-phase liquid crystal material are each long and straight, and they tend to lie parallel with respect to one another, like logs in a river or straws in a broom. They are free to move with respect to one another, and there are some that are at a small acute angle with respect to the "main stream" and a few others that are at any given moment in a position even less consonant with the bulk of the others. A property of the nematic-phase liquid crystal material is that the molecules in the vicinity of a rubbed surface tend to align themselves. Thus, the molecules nearest the surface of the plate 26, for example, are inclined to orient themselves with their long axes parallel to the lines 38 and those nearest the surface of plate 28 are inclined to orient themselves with their long axes parallel to the lines 39. In-between the rubbed surfaces, a twisted structure results; and the effect of this twisted structure on polarized light is to rotate it through 90°. If, however, a potential is applied between the transparent conductive films 30 and 32 as by closing switch 40 (FIG. 2) to apply the potential of battery 42 across the liquid crystal layer 29, the molecules will no longer be parallel to the rubbed surfaces 38 but rather will be normal thereto. This destroys the twisted structure; and the polarized light will no longer be rotated through 90° in passing through the liquid crystal cell.

The effect of the light shutter on polarized light parallel to the lines 38, for example, is that the unit effects a rotation of the plane of polarization of the light as it passes therethrough so that the light emanating from the surface of plate 28 is plane polarized parallel to the lines 39. However, it would not matter if the plane polarized light impinging upon the plate 26, for example, were polarized at some angle with respect to the lines 38. The same effect of rotation of the plane of polarization is obtained. The extent of rotation does not need to be 90°. Any desired extent of rotation may be obtained, merely by properly orienting the unidirectionally rubbed surfaces on the plates 26 and 28. However, when the directions of rubbing are at right angles to each other, the extent of rotation is 90°.

The effect of the liquid crystal unit of FIG. 2 on polarized light is schematically illustrated in FIG. 4. Thus, a source of unpolarized or natural light at 44 impinges on the polarizer 34 which polarizes the light in a plane indicated by the broken lines 46. This polarized light, as it passes through the liquid crystal shutter indicated by the reference numeral 14, such as the unit shown in FIG. 2, will be rotated through 90° so that the polarized light is then polarized in a plane indicated by the broken lines 50. If the polarizer 36 passes polarized light in the plane indicated by the broken lines 52, it can be seen that since the plane of polarization of the light emanating from the unit 14 is at right angles to the plane of polarization of the polarizer 36, no light will pass through and the light shutter will be opaque, or substantially opaque on the order of less than 1% light transmission. The amount of light transmission, however, can be adjusted by rotating either polarizer 34 or polarizer 36.

Now, if an electrical potential is applied across the transparent conductive films 30 and 32 of the light shutter 14, polarized light will no longer be rotated through 90° in passing through the unit. As a result, the polarized light will pass through each of the polarizers 34 and 36 as well as the light shutter 14 and the light shutter will be light-transmitting.

It will be appreciated that by shifting the plane of polarization of polarizer 36 such that it is at 90° to the plane of polarization of polarizer 34, the operation of the device will be reversed. That is, with no potential applied across the transparent conductive films, the polarized light will still be rotated through 90° and will pass through polarizer 36. On the other hand, when a potential is applied and the polarized light is no longer rotated in passing through the cell 14, polarizer 36 will block the light. For safety purposes, the two polarizers utilized in the welding helmet lens assembly are preferably parallel-oriented such that the shutter 14 must be "driven" to a light-transmitting condition by application of a suitable potential across the conducting films. This insures that if there should be a power failure, for example, the shutter will not become light-transmitting in the presence of a welding arc.

The control system for the liquid crystal light shutter 14 utilized in the invention is shown in FIG. 5. The power supply is not shown in FIG. 5. It includes two phototransistors 54 and 56. Each phototransistor 54 and 56 is emitter-coupled to ground through a variable sensitivity resistor 58 or 60, respectively. The phototransistors are also emitter-coupled through amplifiers 62 and 64 to the input of an AND circuit 66. This insures that no output will be derived from the AND circuit 66 until outputs are derived from each of the amplifiers 62 and 64.

Assuming that outputs are derived from the two amplifiers 62 and 64, the AND circuit 66 will produce an output which is applied to an inverter 67 as well as to the input of an oscillator comprising amplifier 68 whose output is also coupled to the input of the inverter 67 as well as through capacitor 70 and resistor 72 to the input of a second amplifier 74. The output of this second amplifier 74 is fed back to the input of amplifier 68 in a positive feedback arrangement so as to produce oscillations at the output of the amplifier 68. The junction of capacitor 70 and resistor 72 is connected as shown through resistor 76 to the input of amplifier 68. The result is that when an output appears from AND circuit 66, oscillations will appear at the output of inverter 67 to apply a field across the liquid crystal cell 14 and thus drive it into a substantially opaque condition.

It will be noted that the one phototransistor 54 is provided with a filter 78 which will pass only visible light; while the phototransistor 56 is provided with a filter 80 which will pass only infrared wave energy. The filter 78, for example, may be a transparent plate having a thin layer of gold on one face, this layer of gold acting to reject infrared wave energy. The infrared filter, on the other hand, may be of the gelatin type. Light from a welding arc 82 will contain both visible and infrared wave energies. Visible wave energies will pass through filter 78 to trigger phototransistor 54 into conduction; while the infrared wave energies from the arc 82 will pass through filter 80 to trigger phototransistor 56 into conduction. When both visible and infrared wave energies are present, outputs will be produced from both of the amplifiers 62 and 64 to drive the liquid crystal light shutter 14 into an opaque condition. However, if only visible or infrared wave energy is present, an output will not be produced from AND circuit 66 and the liquid crystal unit 14 will be light-transmitting.

It can be seen, therefore, that ambient light in a welding shop, in the absence of a welding arc, cannot trigger the liquid crystal unit 14 into an opaque condition since infrared wave energy, or at least insufficient infrared wave energy, is present to trigger phototransistor 56 into conduction. However, when a welding arc is struck with both visible and infrared wave energies present, both phototransistors will conduct and the liquid crystal light shutter 14 will become opaque. On the other hand, when the arc is extinguished and infrared wave energy is still produced by the hot weld bead, the phototransistor 56 will continue to conduct but phototransistor 54 will not since no visible light is present from the arc, and insufficient ambient light is present to trigger the phototransistor 54. Under these conditions, therefore, the liquid crystal light shutter 14 will become light-transmitting even though infrared wave energy is still present. The amounts of infrared and visible wave energies required to trigger phototransistors 54 and 56 are, of course, controlled by the sensitivity resistors 58 and 60.

It can thus be seen that the present invention provides a means for insuring that visible, ambient light will not trigger the liquid crystal lens assembly of the invention into an opaque condition; but at the same time infrared wave energy present after a welding arc is extinguished will not maintain the liquid crystal light shutter in an opaque condition; and the welder can view the work as soon as the arc is extinguished.

Although the invention has been shown in connection with a certain specific embodiment, it will be readily apparent to those skilled in the art that various changes in form and arrangement of parts may be made to suit requirements without departing from the spirit and scope of the invention.

I claim as my invention:

1. In a welding helmet of the type employing a liquid crystal light shutter as a lens assembly, the combination of first means exposed to light emitted from a welding arc for producing a first electrical signal in response only to visible light from said arc, second means exposed to light emitted from a welding arc for producing a second electrical signal only in response to infrared wave energy from said arc, and circuitry coupled to said first and second means and operable only when both said first and second electrical signals are produced for increasing the opacity of the liquid crystal light shutter.

2. The welding helmet of claim 1 wherein the circuitry coupled to said first and second means includes an AND circuit having two inputs and having applied to its two inputs both said first and second electrical signals.

3. The welding helmet of claim 1 wherein the first and second means for producing electrical signals comprise phototransistors, a first filter for light impinging on one of said phototransistors, and a second filter for light impinging on the second of said phototransistors, one of said filters being adapted to pass visible light only and the other being adapted to pass infrared wave energy only.

4. The welding helmet of claim 1 wherein said liquid crystal light shutter comprises a layer of nematic liquid crystal material disposed between transparent parallel plates, transparent conductive films on said plates and in contact with opposite sides of said liquid crystal film, means for effecting a twisted nematic structure in said liquid crystal layer, and parallel polarizers on opposite sides of said transparent parallel plates.

5. The welding helmet of claim 4 wherein said liquid crystal light shutter is normally substantially opaque and becomes light-transmitting only when an electrical field is applied across said liquid crystal material.

* * * * *